United States Patent [19]

Crossley et al.

[11] Patent Number: 4,927,936
[45] Date of Patent: May 22, 1990

[54] QUINOLINE DERIVATIVES

[75] Inventors: Roger Crossley, Reading; Kenneth Heatherington, Burnham, both of United Kingdom

[73] Assignee: John Wyeth and Brother Ltd., Maidenhead, England

[21] Appl. No.: 285,907

[22] Filed: Dec. 16, 1988

Related U.S. Application Data

[63] Continuation-in-part of Ser. No. 571,972, Jan. 18, 1984, Pat. No. 4,837,329.

[30] Foreign Application Priority Data

Jan. 19, 1983 [GB] United Kingdom ............... 8301377

[51] Int. Cl.$^5$ .......................................... C07D 215/04
[52] U.S. Cl. .................................. 546/181; 546/153; 546/157; 546/79
[58] Field of Search ..................... 546/181; 514/311

[56] References Cited

U.S. PATENT DOCUMENTS 4,576,949 3/1986 Smith ................................. 514/277

OTHER PUBLICATIONS

Epsztajn et al., Roczniki Chemii, 43,807 (1969).
Hahn et al., Roczniki Chemii, 38,989 (1964).
Rosen et al., J. Org. Chem. 42,47 (1977).
Dammertz, et al., Arch. Pharm., 313,826 (1980).
Dammertz et al., Arch. Pharm. 314,302 (1981).
Lodde et al., Arch. Pharm. 312,940 (1979).

Primary Examiner—David B. Springer
Attorney, Agent, or Firm—R. K. Jackson

[57] ABSTRACT

The invention concerns a compound formula II

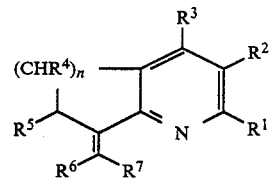

or an acid addition salt thereof, wherein $R^1$, $R^2$, $R^3$, $R^4$, $R^5$, $R^6$, and $R^7$ are the same or different and represent hydrogen, or loweralkyl, cycloalkyl or lower aralkyl, any of which radicals may be substituted by lower alkyl, lower alkoxy or $CF_3$ or phenyl radicals which may be substituted by lower alkyl or $CF_3$ or $R^2$ and $R^3$ taken together, form a 5, 6 or 7 membered saturated ring $R^4$ and $R^5$ may also represent lower alkoxy, or cycloalkoxy, n is 1, 2, or 3 and, if more than one $R^4$ radical is present the $R^4$ radicals may be the same or different with the provisos that (1) when $R^1$, $R^2$, $R^3$, $R^4$, and $R^5$ are all hydrogen, $R^6 R^7$ are not both hydrogen, (2) when $R^1$ and $R^3$ are both phenyl and when $R^1$ is methyl and $R^4$ is methyl then $R^6$ and $R^7$ are not both methyl, and (3) when $R^1$ is hydrogen or methyl, $R^3$ is hydrogen or methyl and $R^2$, $R^4$, $R^5$, and $R^6$ are all hydrogen then $R^7$ is other than unsubstituted phenyl.

The compounds are intermediates for other compounds with anti-ulcer activity.

5 Claims, No Drawings

QUINOLINE DERIVATIVES

The invention relates to quinoline derivatives and is a continuation-in-part of our copending U.S. Ser. No. 571. 972 filed Jan. 18, 1984, U.S. Pat. No. 4,837,329.

In our copending U.S. Ser. No 571972 we have disclosed a process for preparing dihydro compounds of formula I

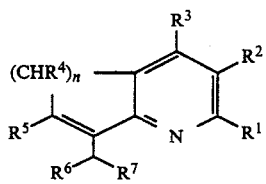

and acid addition salts thereof, wherein $R^1$, $R^2$, $R^3$, $R^4$, $R^5$, $R^6$, and $R^7$ are the same or different and represent hydrogen, or alkyl, cycloalkyl, aralkyl, or aryl radicals any of which radicals may by substituted, or $R^1$ and $R^2$ taken together or $R^2$ and $R^3$ taken together, form a 5, 6 or 7 membered ring which may be saturated or unsaturated and substituted or unsubstituted, $R^4$ and $R^5$ may also represent alkoxy, or cycloalkoxy, n is 1, 2 or 3 and, if more than one $R^4$ radical is present the $R^4$ radicals may be the same or different which process comprises re-arranging a compound of formula II

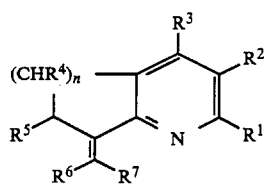

wherein $R^1$, $R^2$, $R^3$, $R^4$, $R^5$, $R^6$, $R^7$ and n are as defined above.

The re-arrangement of compound II to compound I may be carried out under acidic or basic conditions. Examples of acid catalysts which may be used are organic acids such as carboxylic acids e.g. lower alkylcarboxylic acids such as acetic acid, inorganic acids such as phosphoric acid, or polyphosphoric acids, Lewis acids e.g. boron trifluoride, zinc chloride or acid anhydrides e.g. acetic anhydride. Alternatively a noble metal catalyst, e.g. a Pt or Pd catalyst may be used, optionally in the presence of a weak base such as sodium acetate or a heterogeneous or homogeneous catalyst, e.g. $PdCl_2(PhCN)_2$, $RhCl[(C_6H_5)_3P]_3Ru_3(CO)_{12}$ or $IrCl(CO)[(C_6H_5)_3P]_2$.

Preferably the rearrangement is carried out in the presence of acetic acid, a noble metal catalyst in the presence of a base, or a Lewis acid.

The above mentioned acids may be used to prepare acid addition salts of compounds of formula I and other compounds of the invention.

When any of $R^1$, $R^2$, $R^3$, $R^4$, $R^5$, $R^6$, or $R^7$ is an alkyl radical it is preferred that this is a lower alkyl radical of 1 to 6 carbon atoms which may have a straight or branched chain e.g. methyl, ethyl, n- and iso-propyl and n-, s- and t-butyl. When $R^4$ or $R^5$ is an alkoxy radical it is preferred that the radical is lower alkoxy in which the alkyl portion has 1 to 6 carbon atoms and is as defined above, for an alkyl radical.

When any of $R^1$, $R^2$, $R^3$, $R^4$, $R^5$, $R^6$ or $R^7$ is a cycloalkyl radical such radicals having from 4 to 6 carbon atoms are preferred i.e. cyclobutyl, cyclopentyl or cyclohexyl. If $R^4$ or $R^5$ is cycloalkoxy the cycloalkyl portion of this group may be as just described for a cycloalkyl group.

An aralkyl group may be an arylalkyl group in which the alkyl portion is as described herein for an alkyl group. Preferred aralkyl groups are those having from 7–12 carbon atoms.

When any of $R^1$, $R^2$, $R^3$, $R^4$, $R^5$, $R^6$, or $R^7$ is an aryl group it is preferably phenyl or substituted phenyl (substituted by e.g. alkyl, alkoxy or trifluoromethyl). The aryl portion of an aralkyl group may be substituted as described for a phenyl group.

The present invention includes novel compounds of formula II and their acid addition salts wherein $R^1$, $R^2$, $R^3$, $R^4$, $R^5$, $R^6$, and $R^7$ are the same or different and represent hydrogen, or loweralkyl, cycloalkyl or lower aralkyl, any of which radicals may be substituted by lower alkyl, lower alkoxy or $CF_3$ or phenyl radicals which may be substituted by lower alkyl or $CF_3$ or $R^2$ and $R^3$ taken together, form a 5, 6 or 7 membered saturated ring $R^4$ and $R^5$ may also represent lower alkoxy, or cycloalkoxy, n is 1, 2 or 3 and, if more than one $R^4$ radical is present the $R^4$ radicals may be the same or different with the provisos that (1) when $R^1$, $R^2$, $R^3$, $R^4$, and $R^5$ are all hydrogen, $R^6$ and $R^7$ are not both hydrogen, (2) when $R^1$ and $R^3$ are both phenyl and when $R^1$ is methyl and $R^4$ is methyl then $R^6$ and $R^7$ are not both methyl, and (3) when $R^1$ is hydrogen or methyl, $R^3$ is hydrogen or methyl and $R^2$, $R^4$, $R^5$, and $R^6$ are all hydrogen then $R^7$ is other than unsubstituted phenyl.

A preferred sub group of these compounds are those of formula IIA

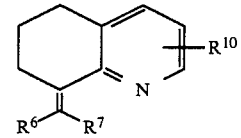

or an acid addition salt thereof wherein $R^{10}$ is lower alkyl and $R^6$ and $R^7$ are selected from hydrogen and lower alkyl. Examples are 5, 6, 7, 8-tetrahydro-3-methyl-8-(2-propylidene)quinoline, 5, 6, 7, 8-tetrahydro-3-methyl-8(methylene) quinoline, and their acid addition salts.

Some compounds of formula II are known. Thus a compound of formula II wherein $R^{1-6}$ are hydrogen, $R^7$ is 3-methoxy phenyl and n is 2 or 3 is disclosed by Dammertz et al Arch.Pharm 313, 826 (1980). A compound of formula II wherein $R^{1-6}$ are hydrogen, $R^7$ is phenyl or 3-methoxyphenyl and n is 3 is disclosed by Dammertz and Reimann Arch. Pharm 314, 302 (1981). A compound of formula II where $R^1$, $R^2$, $R^{4-6}$, are hydrogen, $R^7$ is phenyl, $R^3$ is methyl and n is 2 is disclosed by Lodde and Reiman Arch. Pharm 32, 940 (1979). A compound of formula II wherein $R^1$ is methyl, $R^{2-6}$ are hydrogen, n is 1 or 2 and $R^7$ is phenyl or 3-nitrophenyl is disclosed by Epsztajn et al Roczniki Chemii 1969, 43, 807. A compound of formula II when $R^{1-7}$ are hydrogen and n is 1 or 2 is disclosed by Hahn and Epsztajn, Roczniki Chemii 1964, 38,, 989.

The starting materials of formula II may be prepared by dehydration of the corresponding compound of formula III

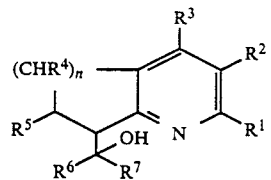

wherein $R^1$, $R^2$, $R^3$, $R^4$, $R^5$, $R^6$, $R^7$ and n are as defined above.

The dehydration may be carried out with usual dehydrating agents e.g. polyphosphoric acid or with acetic anhydride, (in which case an intermediate acetylated derivative may be formed, from which acetic acid is eliminated to give the compound of formula II).

The compounds of formula III may be prepared by treatment of a compound of formula IV

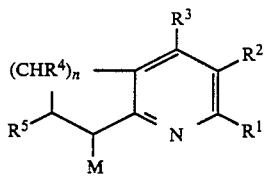

wherein $R^1$, $R^2$, $R^3$, $R^4$, $R^5$ and n as defined in connection with formula I, and M is hydrogen, an alkali metal (e.g. sodium, potassium or lithium) or MgHal, where Hal is chlorine, bromine or iodine, with a carbonyl compound of formula V

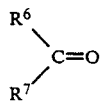

wherein $R^6$, and $R^7$ are as defined in connection with formula I, with the proviso that when $R^6$ and $R^7$ are both hydrogen then M is hydrogen.

It has been reported by Hahn and Epsztajn, Roczniki Chemie, 1964, 38, 989 that treatment of VIa or VIb

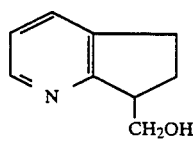

or

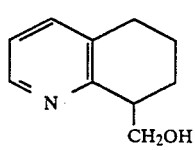

with polyphosphoric acid gives the corresponding methylene compounds VIIa and VIIb

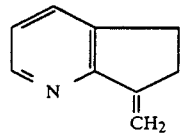

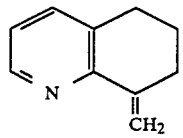

exclusively with no corresponding methyl isomer being formed. We have surprisingly found that compounds of formula I wherein $R^6$ and $R^7$ are hydrogen, can be obtained by treatment of a compound of formula Iv wherein M is hydrogen with formaldehyde (which may be in the form of paraformaldehyde) in the presence of an organic acid anhydride, e.g. acetic anhydride. It is believed that an intermediate compound of formula III wherein $R^6$ and $R^7$ are both hydrogen is formed initially, this dehydrates to give a compound of formula II wherein $R^6$ and $R^7$ are hydrogen and the compound of formula II rearranges to give a compound of formula I wherein $R^6$ and $R^7$ are hydrogen. Previously compounds of formula I were relatively inaccessible—see Rosen and Weber J.Org. Chem. 1977, 42, 47–50 who obtained 8-methyl-5,6-dihydroquinoline by pyrolysis of 1-methyl-1(α-pyridinyl)-1,3-butadiene. However pyrolysis is not a satisfactory method of preparation especially for molecules carrying a variety of substituents.

Compounds of formula II may also be prepared by the Peterson reaction (J Organic Chem 1968, 780; Carey and Toler ibid, 1976, 41, 1956, Hudrik & Peterson J Amer Chem Soc 1975, 97, 1464)—see the scheme below.

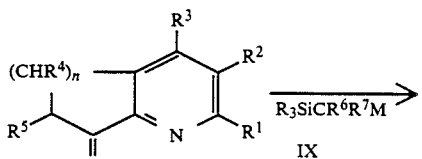

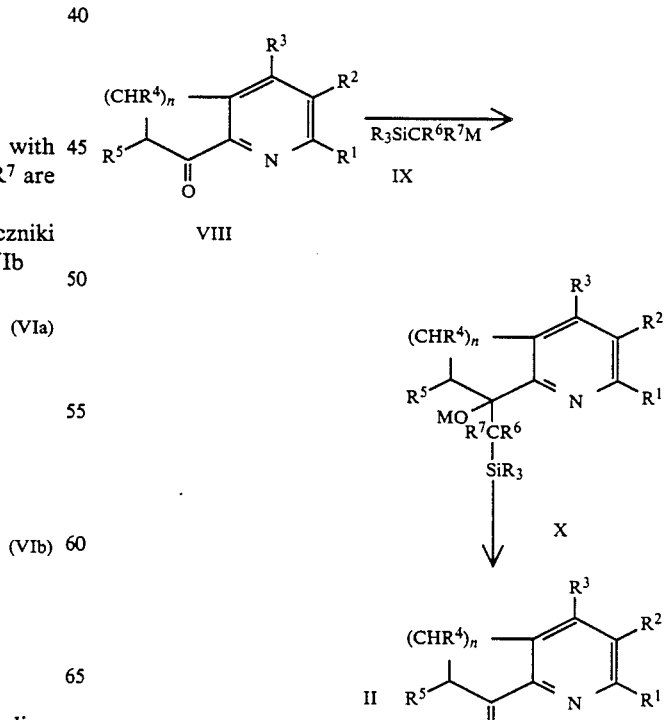

An oxo compound of formula VIII is treated with a silicon compound IX under the conditions of the Peterson reaction to give a silyl compound X which is treated under acidic or basic conditions to give compound II. If the conditions of work up are acidic (e.g. sulphuric acid or trifluoroacetic acid)then compound X will usually be converted first into a compound X where M is H, but basic conditions (e.g. sodium or potassium hydride)and use of fluoride ions (e.g. KF or LiF) usually result in direct formation of compound II. In the silicon compound IX, $R^6$ and $R^7$ are as previously defined in connection with formula I, M is an alkali metal especially lithium or MgHal where Mg denotes magnesium and Hal is chlorine, bromine or iodine, and the three R radicals may be the same or different and alkyl, cycloalkyl, aralkyl or aryl (which radicals may be as previously defined for $R^1$, $R^2$etc. ) or R is selected from electron donating substituents including alkoxy, cycloalkoxy, aralkoxy, aryloxy, alkylthio, cycloalkylthio, aralkylthio or arylthio, the group $R^bR^cN$-wherein $R^b$ and $R^c$ are selected from alkyl, cycloalkyl, aryl and aralkyl (which radicals may be as previously defined for $R^1$, $R^2$ etc.) or $R^b$ and $R^c$ may be joined to form a heterocyclic ring with the nitrogen atom (e.g. a piperidinyl or pyrrolidinyl ring, which may be substituted e.g. by alkyl). It is preferred that $SiR_3$ is triloweralkylsilyl e.g. trimethylsilyl or triarylsilyl e.g.triphenysilyl.

When the R radical is alkoxy or cycloalkoxy these radicals may be as defined above for $R^4$ and $R^5$. Aralkoxy and aryloxy radicals for R may be such radicals in which the aralkyl or aryl portions are as defined above for aralkyl or aryl radicals. Similarly when R radicals are alkylthio, cycloalkylthio, aralkylthio, or arylthio, the alkyl, cycloalkyl, aralkyl or aryl portions of these radicals may be as defined above for alkyl, cycloalkyl, aralkyl or aryl radicals.

The silicon compound IX starting materials may be prepared from corresponding compounds $R_3SiCHR^6R^7$ by standard methods. The starting materials of formula VIII may be prepared as described in UK Patent Specification No. 1460457 or by analogous methods.

In a variation of the above reaction the compounds of formula II may be prepared by the following scheme:

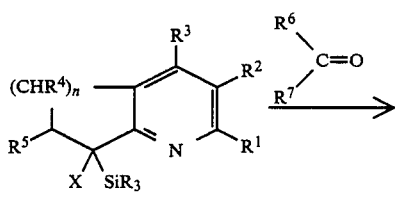

XI

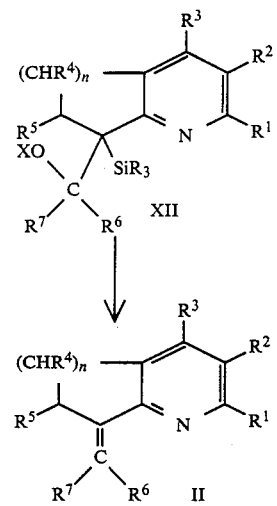

A silicon compound of formula XI, where $R^1$, $R^2$, $R^3$, $R^4$, $R^5$, R and n are as previously defined and X is hydrogen, sodium potassium or lithium is reacted with a carbonyl compound $R^6R^7CO$ to obtain a silyl intermediate of formula XII which is converted to compound II by acid or base treatment as described for the previous reaction scheme. The starting compound XI may be prepared as described in U.S. patent application Ser. No. 506277 filed June 21, 1983, or by analogous methods. Briefly a compound of formula

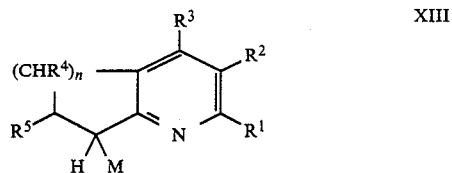

where M is sodium, potassium or lithium is treated with a silylating agent of formula $R_3SiHal$ where R is as defined above and Hal is chlorine, bromine or iodine, to obtain a compound of formula XI wherein X is hydrogen and if desired treating this with a metal compound $R^*M$ where M is sodium, potassium or lithium and $R^8$ is alkyl, cycloalkyl, aralkyl or aryl or an amine residue to obtain a compound of formula XI where X is sodium, potassium or lithium.

Alternatively compounds of formula II may be prepared by the Wittig reaction (see Peterson loc cit for references thereto).

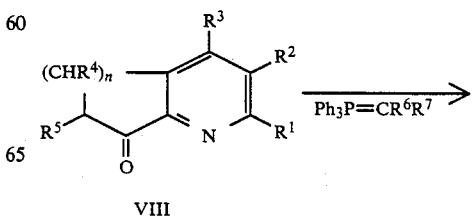

VIII

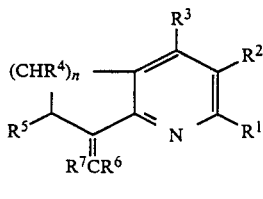

The Wittig phosphorus reagent is prepared by reacting Ph₃P with a compound R⁶R⁷CHBr.

Compounds of formula I may be used as intermediates for the preparation of the corresponding compounds of formula XIV

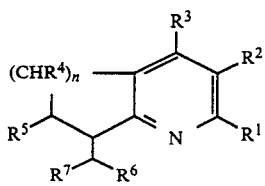

Compounds of formula XIV are intermediates for other compounds with anti-ulcer or anti-secretory activity e.g. the compounds of UK Patent Specification No. 1432378.

Compounds of formula II, where R⁶ and/or R⁷ are phenyl or substituted phenyl may also posses anti-inflammatory activity as determined by standard test procedures. The invention is illustrated by the following Examples.

EXAMPLE 1

3,8-Dimethyl-5,6,7,8-tetrahydroquinoline

A mixture of 3-methyl-5,6,7,8-tetrahydroquinoline (100 ml) paraformaldehyde (30 g) and acetic anhydride (100 ml) was heated at reflux or 30 hours. The residue was distilled to give a mixture of starting tetrahydroquinoline and 3,8-dimethyl-5,6-dihydroquinoline (40 g) bp. 126–180°/15 mm. Chromatography on silica gel (500 g, Woelm active, 100–200) using di-isopropyl ether gave 3,8-dimethyl-5,6-dihydroquinoline (22g).

A solution of the dihydroquinoline (22 g) in ethanol (200 ml) was hydrogenated over 10% palladium on carbon (1 g) at 25° and 1 atmosphere. After the theoretical uptake had occurred (1.5 hours) the catalyst was removed by filtration, the filtrate evaporated and the residue distilled to give the title tetrahydroquinoline (22 g) bp. 124°/15 mm C₁₁H₁₅N requires: C,81.9; H,9.4; N,8.7%. Found: C, 81.9, H,9.1, N,8.3%.

The catalyst in this example is a mixture of acetic anhydride and acetic acid, the acetic acid being produced in situ.

EXAMPLE 2

Compound Present

The reaction described in Example 1, 1st paragraph, was followed in a time course experiment, samples being taken at intervals and composition analysed by glc. (Pye 104 C20M T=200°) Results were as follows:

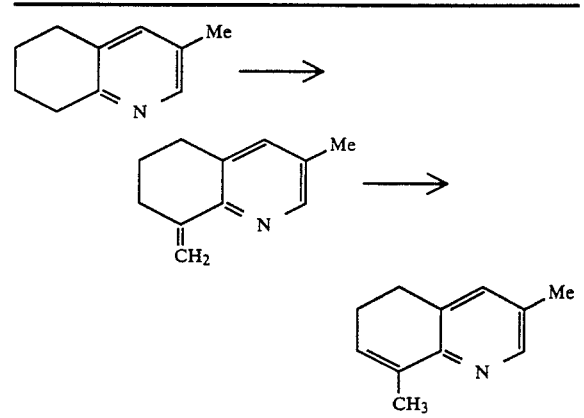

| Starting Material (A) Time | (B) | (C) |
|---|---|---|
| 1½ hours 20% | 66% | 7% |
| 2½ hours 21% | 61% | 11% |
| 4½ hours 22% | 51% | 20% |
| 6½ hours 23% | 42% | 26% |
| 30 hours 22% | 0 | 68% |

EXAMPLE 3

The reaction described in Example 1, 1st paragraph, was repeated employing various catalysts. The results are shown in the following table (for structures of compounds B and C—see Example 2).

Isomerisation of Compound B to Compound C using various Catalysts.

| Catalyst/Reaction Conditions | Reaction time (hours) | Percentage of Compound C |
|---|---|---|
| CH₃CO₂H, reflux | 30 | 100 |
| NaOAc, 5% Pd—C, EtOH, reflux | 21.6 | 85.4 |
| BF₃—Et₂O, dioxan, reflux | 24 | 83 |
| PPA, 100° | 1.5 | 76ᵃ |
| H₃PO₄, H₂O, reflux | 21.6 | 25.1 |
| ZnCl₂, dioxan, reflux | 30 | 22.5 |
| (CH₃CO)₂O, reflux | 30 | 5 |
| KOH, EtOH, 22° | 30 | 5 |

ᵃSevere decomposition of compound C was observed after 2 hours.
PPA = Polyphosphoric acid

EXAMPLE 4

[8R*]-5,6,7,8-tetrahydro-8-([2S*])-2-(2-hydroxy-1-phenyl) propyl)-3-methylquinoline.

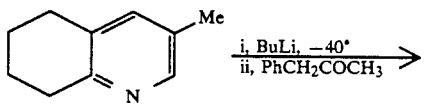

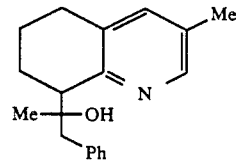

To a mixture of 5,6,7,8-tetrahydro-3-methylquinoline (20 g) and toluene (100 ml) was added 1.63 molar n-

BuLi in hexane (93 ml) at −40° C. The resulting anion solution was added to a mixture of phenylacetone (50 ml) and toluene (100 ml) at −40° C. The solution was allowed to warm to room temperature and the excess n-BuLi was quenched by adding 2N HCl (90 ml). The excess solvent was removed by evaporation. The resultant aqueous mixture was basified with saturated aqueous NaHCO$_3$ solution and extracted with EtOAc (3×100 ml). The extracts were dried (MgSO$_4$) and the solvent removed by evaporation. The mixture of products was separated by chromatography[SiO$_2$; cyclohexane —CH$_3$CO$_2$CH$_3$ (4:1)]. Upon removal of the solvent by evaporation the product crystallised to give the title compound (2.25 g), m.p. 99°–101° C. (Found: C,81.1; H,8.1; N,4.7. C$_{19}$H$_{23}$NO requires C,81.1; H,8.2; N,5.0%).

EXAMPLE 5

[8R*]-5,6,7,8-tetrahydro-8-([2R*]-2-(2-hydroxy-1-phenyl) propyl)-3-methylquinoline

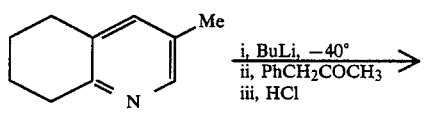

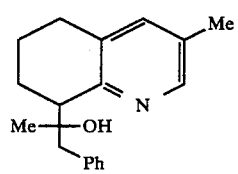

To a mixture of 5,6,7,8-tetrahydro-3-methylquinoline (20 g) and toluene (100 ml) was added 1.63 molar n-BuLi in hexane (93 ml) at −40° C. The resulting anion solution was added to a mixture of phenylacetone (50 ml) and toluene (100 ml) at −40° C. The resulting solution was allowed to warm to room temperature. The excess n-BuLi was quenched by adding 2N-HCl (90 ml). The aqueous layer was separated, basified with saturated aqueous NaHCO$_3$ solution, and extracted with Et$_2$O (3×100 ml). The ethereal extracts were dried (MgSO$_4$) and the solvent removed by evaporation. The mixture of products was separated by chromatography [SiO$_2$; cyclohexane—methyl acetate (80:20)]. The solvent was removed by evaporation and the residue dissolved in Et$_2$O, to which an ethereal solution of HCl (50 ml) was added. The precipitate was collected by filtration, washed with Et$_2$O, and dried in vacuo to give the title compound as a hydrochloride 1½ hydrate (2.09 g) m.p. 98°–100° C. (Found: C,66.2; H,7.5; N,3.9. C$_{19}$H$_{23}$NO. HCl 3/2. H$_2$O requires C,66.2; H,7.9; N,4.1%).

EXAMPLE 6

5,6,7,8-tetrahydro-8-(1-hydroxyethyl)-3-methylquinoline

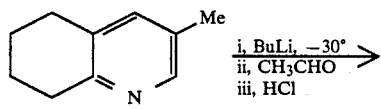

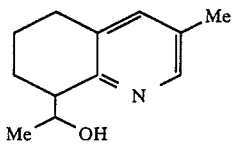

To a mixture of 5,6,7,8-tetrahydro-3-methylquinoline (20 g) and dry THF (150 ml) was added 1.63 molar n-BuLi in hexane (108 ml) at −30° C. The resulting anion solution was added to a solution of acetaldehyde (50 ml) in anhydrous THF (50 ml) at −30° C. The solution was allowed to warm to room temperature. The excess n-BuLi was quenched with 2N-HCl (20 ml). The excess acetaldehyde and solvent were removed by evaporation. The resultant aqueous mixture was basified with saturated aqueous NaHCO$_3$ solution and extracted with Et$_2$O (3×100 ml). The ethereal extracts were dried (MgSO$_4$) and the solvent removed by evaporation. The mixture of products was separated by chromatography (SiO$_2$; EtOAc). The solvent was removed by evaporation and the residue dissolved in Et$_2$O to which ethereal HCl (50 ml) was added. The product was removed by filtration, washed with Et$_2$O and dried in vacuo to give the title compound as the hydrochloride ¼ hydrate (1.13 g) m.p. 172°–175° C. (Found: C,62.4; H,7.9; N,6.0 C$_{12}$H$_{17}$NO. HCl. ¼H$_2$O requires C,62.1; N,8.0; N,6.0%).

EXAMPLE 7

5,6,7,8-Tetrahydro-8-(2(2-hydroxy)propyl)-3-methylquinoline

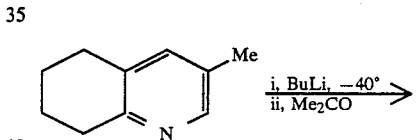

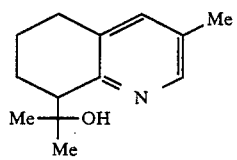

To a mixture of 5,6,7,8-tetrahydro-3-methylquinoline (23.44 g, 159 mmol) and toluene (200 ml) was added 1.63 molar n-BuLi in hexane (108 ml) at −40°. After 15 mins. the resulting anion solution was added to a solution of acetone (100 ml) in toluene (200 ml). The solution was allowed to warm to room temperature and was treated with 2N-HCl (90 ml). The excess acetone was removed by evaporation in vacuo. The resultant aqueous mixture was basified with saturated aqueous NaHCO$_3$ solution and extracted into Et$_2$O (3×100 ml). The ethereal extracts were dried (MgSO$_4$) and the solvent removed by evaporation in vacuo. The mixture of products were separated by chromotography [SiO$_2$; EtOAc-petrol (1:4)] to give the free base (7.303g, 22%) of the title compound as a red oil.

A small quantity of the free base (0.744 g) was dissolved in Et$_2$O and treated with ethereal HCl. The product was removed by filtration, washed with Et$_2$O, and dried in vacuo to give the title compound as the hydrochloride, m.p. 140°–144°. (Found: C,63.2; H,B.3;

N,5.5. $C_{13}H_{19}NO \cdot HCl \cdot \tfrac{1}{4}H_2O$ requires C,63.4; H,8.4; N,5.7%).

EXAMPLE 8

5,6,7,8-Tetrahydro-3-methyl-8-(2-propylidene)quinoline

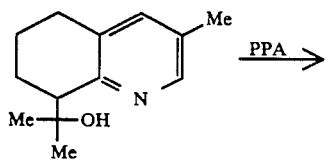

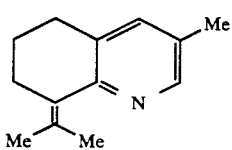

Experimental Details

A mixture of 5,6,7,8-tetrahydro-8-(2(2-hydroxy) propyl)-3-methylquinoline (3.044 g, 14.8 mmol) and polyphosphoric acid (20g) was vigorously stirred at 80°–90° for 50 mins. and then poured into saturated aqueous Na₂CO₃ solution (200 ml). The aqueous solution was extracted with Et₂O (2×100 ml) and the ethereal extracts dried (MgSO₄) and evaporated in vacuo to give an oil. Purification by column chromatography [SiO₂; hexane-propan-2-ol (1:1)] and bulb-to-bulb distillation gave the title compound (1.855 g,67%) as a colourless oil, b.p. 150°–155°/0.1 mm Hg (Found: C,83.25; H,9.3; N,7.5 $C_{13}H_{17}N$ requires C,83.4; H,9.15; N,7.5%).

We claim:

1. A compound of formula II

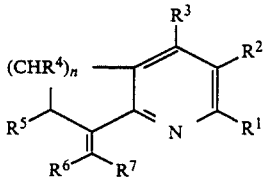

or a pharmaceutically acceptable salt thereof, wherein $R^1$, $R^2$, $R^3$, $R^4$, $R^5$, $R^6$ and $R^7$ are, independently, hydrogen, or alkyl of 1 to 6 carbon atoms, cycloalkyl of 4 to 6 carbon atoms or aralkyl of 7 to 12 carbon atoms, any of which radicals may be monosubstituted by alkyl or 1 to 6 carbon atoms, alkoxy of 1 to 6 carbon atoms, or —CF₃ or phenyl radicals which may be monosubstituted by alkyl of 1 to 6 carbon atoms or —CF₃;

or $R^2$ and $R^3$, taken together, form a 5, 6 or 7 membered saturated carbocyclic ring;

$R^4$ and $R^5$ may also be alkoxy of 1 to 6 carbon atoms or cycloalkoxy of 4 to 6 carbon atoms;

n is one of the integers 1, 2 or 3;

and, if more than one $R^4$ group is present, the $R^4$ groups may be the same or different;

with the provisos that (1) when $R^1$, $R^2$, $R^3$, $R^4$, and $R^5$ are all hydrogen, $R^6$ and $R^7$ are not both hydrogen, (2) when $R^1$ and $R^3$ are both phenyl and when $R^1$ is methyl and $R^4$ is methyl, $R^6$ and $R^7$ are not both methyl, and (3) when $R^1$ is hydrogen or methyl, $R^3$ is hydrogen or methyl and $R^2$, $R^4$, $R^5$, and $R^6$ are all hydrogen, then $R^7$ is other than unsubstituted phenyl.

2. A compound of formula II, as claimed in claim 1, wherein n is 2 and $R^1$, $R^2$, $R^3$, $R^4$, and $R^5$ are selected from hydrogen and alkyl of 1 to 6 carbon atoms.

3. A compound of formula IIa

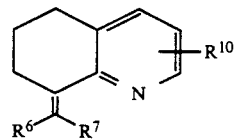

or an acid addition salt thereof wherein $R^{10}$ is lower alkyl of 1 to 6 carbon atoms and $R^6$ and $R^7$ are selected from hydrogen and lower alkyl of 1 to 6 carbon atoms.

4. 5, 6, 7, 8-Tetrahydro-3-methyl-8-(2-propylidene) quinoline or an acid addition salt thereof.

5. 5, 6, 7, 8-Tetrahydro-3-methyl-8(methylene) quinoline or an acid addition salt thereof.

* * * * *